(12) United States Patent
Schildkraut et al.

(10) Patent No.: US 9,974,503 B2
(45) Date of Patent: May 22, 2018

(54) SYSTEM FOR PARANASAL SINUS AND NASAL CAVITY ANALYSIS

(75) Inventors: Jay S. Schildkraut, Rochester, NY (US); Lawrence A. Ray, Rochester, NY (US); Krishnamoorthy Subramanyan, Palatine, IL (US)

(73) Assignee: Carestream Dental Technology Topco Limited, London (GB)

( * ) Notice: Subject to any disclaimer, the term of this patent is extended or adjusted under 35 U.S.C. 154(b) by 0 days. days.

(21) Appl. No.: 14/131,694

(22) PCT Filed: Jun. 12, 2012

(86) PCT No.: PCT/US2012/042005
§ 371 (c)(1),
(2), (4) Date: Jan. 21, 2014

(87) PCT Pub. No.: WO2013/012492
PCT Pub. Date: Jan. 24, 2013

(65) Prior Publication Data
US 2014/0330115 A1  Nov. 6, 2014

Related U.S. Application Data

(60) Provisional application No. 61/510,187, filed on Jul. 21, 2011.

(51) Int. Cl.
*A61B 6/00* (2006.01)
*A61B 6/03* (2006.01)
(Continued)

(52) U.S. Cl.
CPC .............. *A61B 6/463* (2013.01); *A61B 6/032* (2013.01); *A61B 6/4085* (2013.01); *A61B 6/466* (2013.01);
(Continued)

(58) Field of Classification Search
CPC ....... A61B 6/032; A61B 6/4085; A61B 6/463; A61B 6/466; A61B 6/469; A61B 6/501;
(Continued)

(56) References Cited

U.S. PATENT DOCUMENTS

| 2006/0084860 A1* | 4/2006 | Geiger et al. ................. 600/407 |
| 2007/0173724 A1 | 7/2007 | Singh |
| 2007/0255161 A1 | 11/2007 | De Backer |
| 2008/0031408 A1 | 2/2008 | Sukovic et al. |
| 2011/0227910 A1* | 9/2011 | Ying et al. ..................... 345/419 |

FOREIGN PATENT DOCUMENTS

WO  2009/120196  10/2009

OTHER PUBLICATIONS

Erkan Tarhan et al., "Acoustic rhinometry in humans: accuracy of nasal passage area estimates, and ability to quantify paranasal sinus volume and ostium size," Journal of Applied Physiology, Aug. 1, 2005, vol. 99, No. 2, pp. 616-623.

(Continued)

*Primary Examiner* — Michael Rozanski

(57) ABSTRACT

A method for displaying a paranasal sinus region of a patient is executed at least in part on a computer, acquiring volume image data of the paranasal sinus region of the patient, identifying one or more airways within the paranasal sinus region from the volume image data, displaying the at least one or more airways, and highlighting one or more portions of the displayed airways that are constricted below a predetermined value.

23 Claims, 16 Drawing Sheets

(51) Int. Cl.
*G06T 19/20* (2011.01)
*G06T 7/11* (2017.01)

(52) U.S. Cl.
CPC .............. *A61B 6/469* (2013.01); *A61B 6/501* (2013.01); *A61B 6/5217* (2013.01); *A61B 6/5223* (2013.01); *G06T 7/11* (2017.01); *G06T 19/20* (2013.01); *A61B 6/506* (2013.01); *G06T 2200/04* (2013.01); *G06T 2207/10081* (2013.01); *G06T 2207/20044* (2013.01); *G06T 2207/30172* (2013.01); *G06T 2210/41* (2013.01); *G06T 2219/2012* (2013.01)

(58) Field of Classification Search
CPC ..... A61B 6/506; A61B 6/5217; A61B 6/5223; G06T 19/20; G06T 2200/04; G06T 2200/2207; G06T 2200/10081; G06T 2200/20044; G06T 2200/30172; G06T 2210/41; G06T 2219/2012; G06T 7/0081
See application file for complete search history.

(56) References Cited

OTHER PUBLICATIONS

International Search Report for International Application No. PCT/US2012/042005 dated Mar. 29, 2013, 3 pages.

T. N. Pappas "An Adaptive Clustering Algorithm for Image Segmentation," *IEEE Transactions on Signal Processing*, vol. 40, 1992., p. 901-914.

Shi, Scarfe, Farman, "Maxillary sinus 3D segmentation and reconstruction from cone beam CT data sets", *International Journal of Computer Assisted Radiology and Surgery*, 2006, vol. 1, No. 2, 7 pages.

Dastidar, Heinonen, Numminen, Rautiainen, Laasonen, "Semi-automatic segmentation of computed tomographic images in volumetric estimation of nasal airway", *European Archives of Oto-Rhino-Laryngology*, 1999, vol. 256, No. 4, pp. 192-198.

* cited by examiner

710

SYSTEM FOR PARANASAL SINUS AND NASAL CAVITY ANALYSIS

FIELD OF THE INVENTION

The invention relates generally to the field medical imaging systems and in particular to systems that process and display images of the paranasal sinus region, including the nasal cavities.

BACKGROUND

The paranasal sinuses are air-filled regions within bones of the skull. Specifically, the frontal, ethmoid, maxilla, and sphenoid bones contain sinuses that are named for the bone structure that immediately surrounds them. In addition, the nasal region contains smaller bones including the inferior turbinate, lacrimal, palatine, and nasal bones. The spaces between these articulated bones are sometimes air filled. The bones of the sinus and nasal cavities are covered by a mucosa lining, producing mucus that drains into the nasal cavity and subsequently into the throat. A sinus cell is connected to the nasal cavity by a narrow opening called the ostium. The arrangement of sinus cells and bones forms paths for drainage. When drainage is prevented by constriction or blockage of the ostia and/or paths, sinusitis, infection or inflammation in the paranasal sinus region, can result.

The condition of the paranasal sinuses and nasal cavity can be assessed using an X-ray computerized tomographic (CT) image of a patient's head, at the level of the sinuses. Image acquisition for this purpose is generally performed with a fan-beam computed tomographic system (FBCT) or a conebeam computed tomographic (CBCT) system. However, the anatomy of the paranasal sinuses is very complicated, making it difficult to interpret images of the paranasal region and to detect problem conditions. As a further complication, the anatomy of the sinuses and bones of the nasal region can vary significantly from patient to patient. Furthermore, pathological conditions can greatly alter the anatomy of the sinuses and nasal cavity. For these reasons, it can be difficult even for a skilled practitioner to determine the condition and drainage paths for each sinus by examination of the axial, coronal, sagittal, and other views of the CT image.

Thus, there is a need for apparatus and methods for analysis and display of the paranasal sinus region, including nasal cavity structures, and for display of related drainage path information.

SUMMARY

It is an object of the present invention to advance the art of medical imaging to allow improved analysis and display of the paranasal sinus region. A related object of the present invention is to assess and display drainage paths through the sinuses and to indicate areas of potential blockage, relatively high curvature, or other problem.

It is an object of the present invention to provide a system that automatically determines the condition and connections of the airways that are comprised of the paranasal sinuses, nasal cavity, and throat. It is also an object of this invention to quantify features such as the dimensions of the sinuses, ostia, and paths through which mucus drainage occurs. In addition, it is an object of this invention to determine the anatomy of the paranasal sinus region with attention to anatomical variations. Furthermore, it is the object of this invention to display information to a user that provides improved understanding of the condition, location, connections, paths, drainage, and anatomy of the paranasal sinus region, including the nasal cavities.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method for displaying a paranasal sinus region of a patient, the method executed at least in part on a computer and comprising: acquiring volume image data of the paranasal sinus region of the patient; identifying one or more airways within the paranasal sinus region from the volume image data; displaying the at least one or more airways; and highlighting one or more portions of the displayed one or more airways that are constricted below a predetermined value.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 13 shows one type of computer apparatus for performing the processing of the present invention.

DETAILED DESCRIPTION

Figure 1:
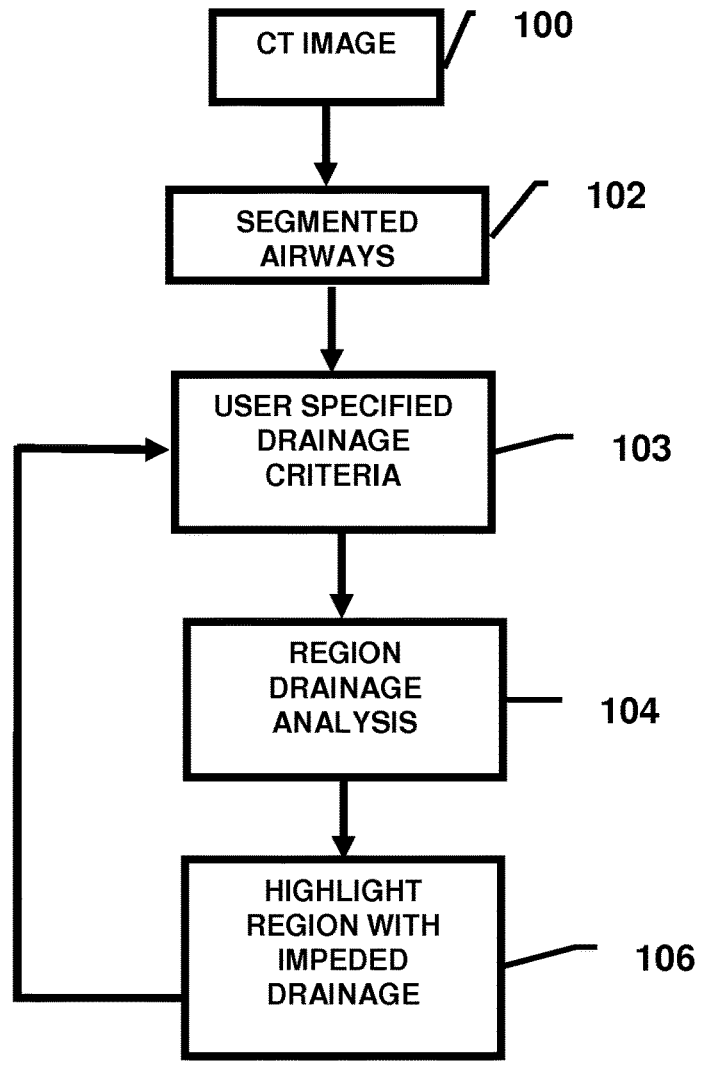
FIG. 1 is a logic flow diagram that shows a process for detection and display of drainage in paranasal and nasal cavity analysis.

The following is a detailed description of the preferred embodiments of the invention, reference being made to the drawings in which the same reference numerals identify the same elements of structure in each of the several figures.

In the context of the present disclosure, the paranasal sinus region includes the nasal cavity, paranasal sinuses, and all or part of associated bones including the frontal, maxilla, ethmoid, sphenoid, inferior turbinate, middle turbinate, superior turbinate, lacrimal, nasal, and palatine bones. Also, for the purpose of the present disclosure, the term "airways" includes the mouth, throat, nasal cavity, maxillary, ethmoid, sphenoid, frontal paranasal sinuses, and other air-filled regions that are internal to the head.

In the context of the present disclosure, the term "image" refers to multi-dimensional image data that is composed of discrete image elements. For 2-D images, the discrete image elements are picture elements, or pixels. For 3-D images, the discrete image elements are volume image elements, or voxels.

In the context of the present disclosure, the term "code value" refers to the value that is associated with each volume image data element or voxel in the reconstructed 3-D volume image. The code values for CT images are often, but not always, expressed in Hounsfield units.

The term "highlighting" for a displayed feature has its conventional meaning as is understood to those skilled in the information and image display arts. In general, highlighting uses some form of localized display enhancement to attract the attention of the viewer. Highlighting a portion of an image, such as an individual organ, bone, or structure, or a path from one chamber to the next, for example, can be achieved in any of a number of ways, including, but not limited to, annotating, displaying a nearby or overlaying symbol, outlining or tracing, display in a different color or at a markedly different intensity or gray scale value than other image or information content, blinking or animation of a portion of a display, or display at higher sharpness or contrast.

One aspect of this invention is described with reference to the flow diagram of FIG. 1. In an acquisition step 100, a CT image of the paranasal sinus region is acquired. This image data may be acquired with a fan-beam or cone beam CT scanner. Preferably, because of its improved resolution and overall image quality, the CT scan is acquired with a cone beam CT (CBCT) scanner. A 3D image of the sinus region is reconstructed with isotropic voxels. In a segmentation step 102, the airways in the CT image are segmented. In the segmentation process, consistent with one embodiment of the present invention, each voxel in the 3D tomographic image data is assigned to a class. In one embodiment, the assignment of a class to a voxel is, at least in part, dependent on the code value of one or more neighboring or adjacent voxels in the volume image data. In an alternate embodiment, the assignment of a class to a voxel is, at least in part, dependent on the class assignment of one or more neighboring or adjacent voxels in the volume image data. For segmentation of medical images, possible classes include air, water, bone, muscle, adipose, and other types of tissue or implant material. In airways segmentation, voxels in the 3D image that correspond to air that is internal to the head have the air class assigned to them. In an alternate embodiment, airway segmentation can be performed using any of a number of suitable image segmentation methods known to those skilled in the image processing arts. Candidate segmentation methods include, but are not limited to, K-means clustering, adaptive K-means clustering, region growing, fast-marching, level set, thresholding, graph partitioning, model based, compression based, edge-based, classifier, and watershed segmentation methods, or combinations of these and other methods, adapted to the parameters and requirements of airways segmentation.

In a step 103 of FIG. 1, the user specifies criteria for drainage paths between regions of the airways. For example, the user may specify that the minimum effective path diameter between regions must be greater than 1.0 mm. The user may alternately specify that as long as there is any connection between airway regions, no matter how small, a drainage path exists. There may also be default criteria for displaying areas of constriction used in step 103, obviating the need for user-entered criteria prior to display of the sinus regions. In an analysis step 104, the segmented airways are analyzed to determine regions for which there are drainage paths that satisfy the criteria of step 103. In a display step 106, a region of the airways for which drainage is impeded based on the criteria of step 103 is displayed to the user, such as in a highlight color different from other parts of segmented airways. If the display device does not support color, or if desired for other reasons, different shades of gray or texture patterns can alternately be used to highlight or distinguish a region with impeded drainage. One or more symbols or outlining can alternately be used to indicate constriction. The system may then return to step 103 in which the drainage criteria are modified, which may result in a change in the color or other presentation of regions that are displayed to the user.

Figure 2:
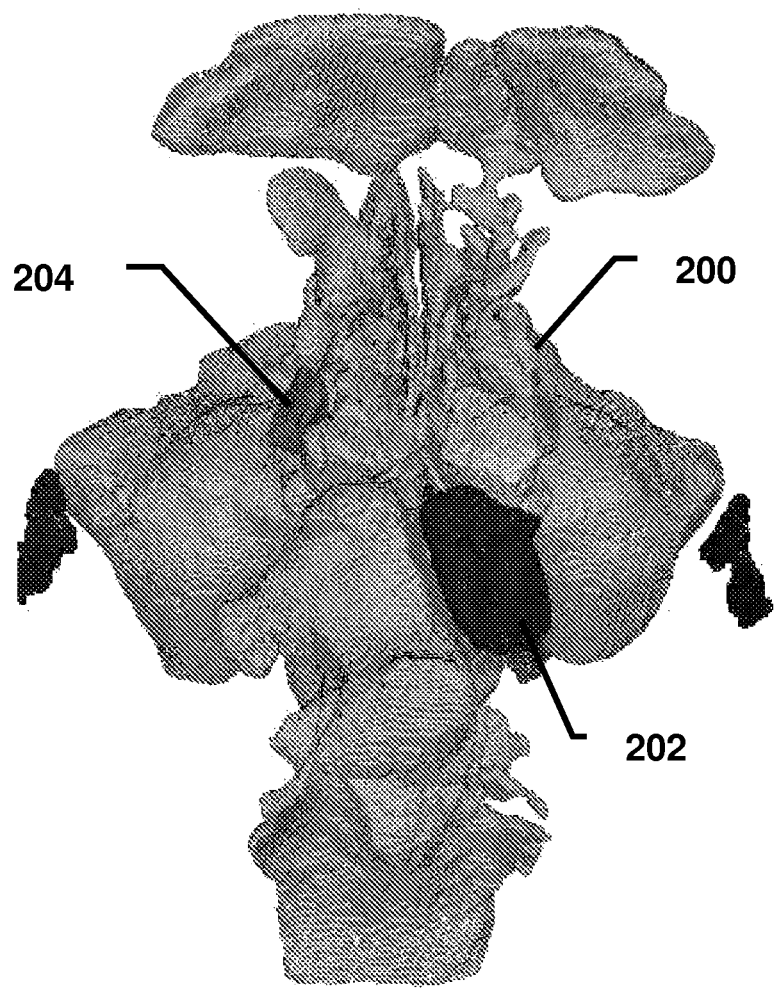
FIG. 2 is a view of a paranasal and nasal cavity volume showing different structures.

The display of FIG. 2 shows, by way of example, the result of applying the method of FIG. 1 to a CT image of the sinus region. As illustrated by FIG. 2, the user is informed by the system of the present invention of impeded drainage for two sinus cells according to the drainage criteria of step 103 in FIG. 1. In this figure, a main region 200 includes the main part of the airways, which includes the throat, nasal cavity, and most of the nasal sinuses. A right sphenoid sinus 202 is shown in a different shade of gray, thereby indicating that its drainage to other parts of the airways is impeded. A cell 204 of the left ethmoid sinus is also highlighted, such as by being displayed in another color or shade of gray, again indicating impeded drainage to other parts of the airways. By highlighting constricted or otherwise affected regions of the paranasal region and related sinus structures this way, the system informs the user that mucus drainage from sinus cells to the nasal cavity and throat is prevented and shows the approximate location of the blockage. This can assist to diagnose sinus problems including sinusitis.

Figure 3:
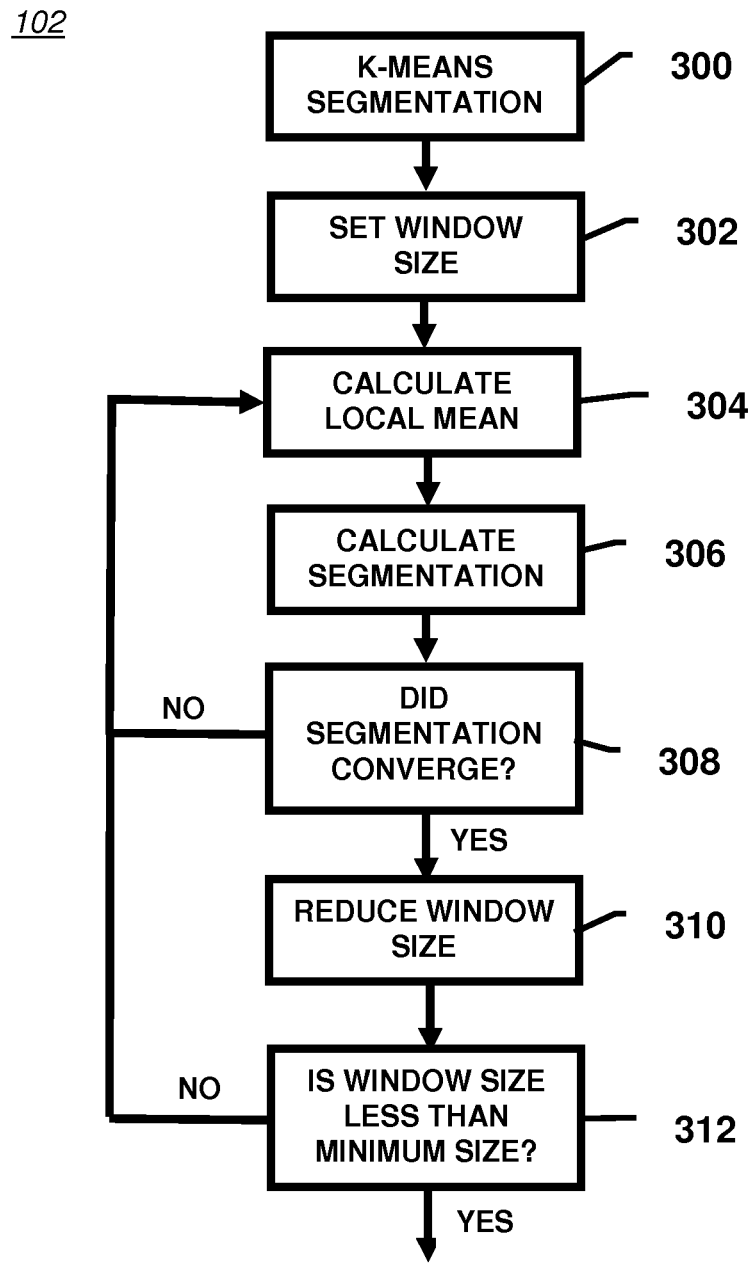
FIG. 3 is a logic flow diagram that shows adaptive segmentation processing according to an embodiment of the present invention.

Segmentation of the airways is difficult because they are comprised of both large air filled volumes, for example the throat and maxillary sinuses, and small air filled cavities such as the regions between the nasal turbinates and the wall of the nasal cavity and septum. Also, partial volume effects and tomographic reconstruction artifacts that arise from X-ray scattering, beam hardening, and other sources result in variation of the code value of air in different parts of the airways. For these reasons, embodiments of the present invention use an adaptive segmentation method in airways segmentation step 102 of FIG. 1. The flow diagram of FIG. 3 shows an adaptive segmentation step 102 that is used according to an embodiment of the present invention. This method is based on "An Adaptive Clustering Algorithm for Image Segmentation," by T. N. Pappas in *IEEE Transactions*

*on Signal Processing*, Vol. 40, 1992. In a segmentation step 300 of FIG. 3, global K-means segmentation is performed on the CT image. In this step, the mean code value for each cluster is global, which means that it does not vary with location within the image. According to one embodiment of the present invention, the number of clusters (value of K) is set to 4, although other values could alternately be used. The result of step 300 is a rough segmentation of the image into air, low density soft tissue, high density soft tissue, and bone clusters. Low density soft tissue is mostly comprised of adipose and high density tissue of muscle.

Continuing with the process of FIG. 3, a window selection step 302 sets a spatial window size. For example, a 13×13×13 voxel window is selected. In a calculation step 304, for each cluster, the local mean code value is calculated at each voxel in the CT image within the window that is centered at the voxel. The local cluster mean can then be modified by setting it equal to a weighted average of the local and global cluster mean in order to prevent the local mean from deviating excessively from its global value. In a voxel assignment step 306, each voxel in the image is assigned to a cluster. This assignment is partially based on the difference between the voxel's code value and the local mean of each cluster. In addition, voxel cluster assignment is also based on the cluster assigned to neighboring voxels, in order to impose a degree of spatial smoothness on the segmented airways. Steps 304, 306, and 308 repeat until the assignment of voxels to a cluster is unchanged or cluster assignment has changed for only a small number of voxels. In a step 310, the window size is reduced and the method returns to step 304. The segmentation process ends when the window size is less than a set minimum window size, as determined in a decision step 312.

The final result of the method in FIG. 3 is a cluster map in which each voxel in the CT image is assigned the number of the cluster to which it belongs. Since each cluster is associated with a class of material, the cluster map is also a type of class map in which each voxel of the image has a class assigned to it. The cluster with the lowest mean code value is then the cluster that corresponds to the air class. When all voxels of the cluster map that belong to the air class are set to 1 and all other voxels are set to 0 the result is an air segmentation map of both external ambient air and airways that are internal to the head. The external air is removed from the segmentation map by creating a tissue map that is comprised of non-air class voxels. Morphological closing and flood-fill operations are then used to close holes in the tissue map. The intersection of this modified tissue map and air segmentation map is the final map of the segmented airways.

Figure 4:
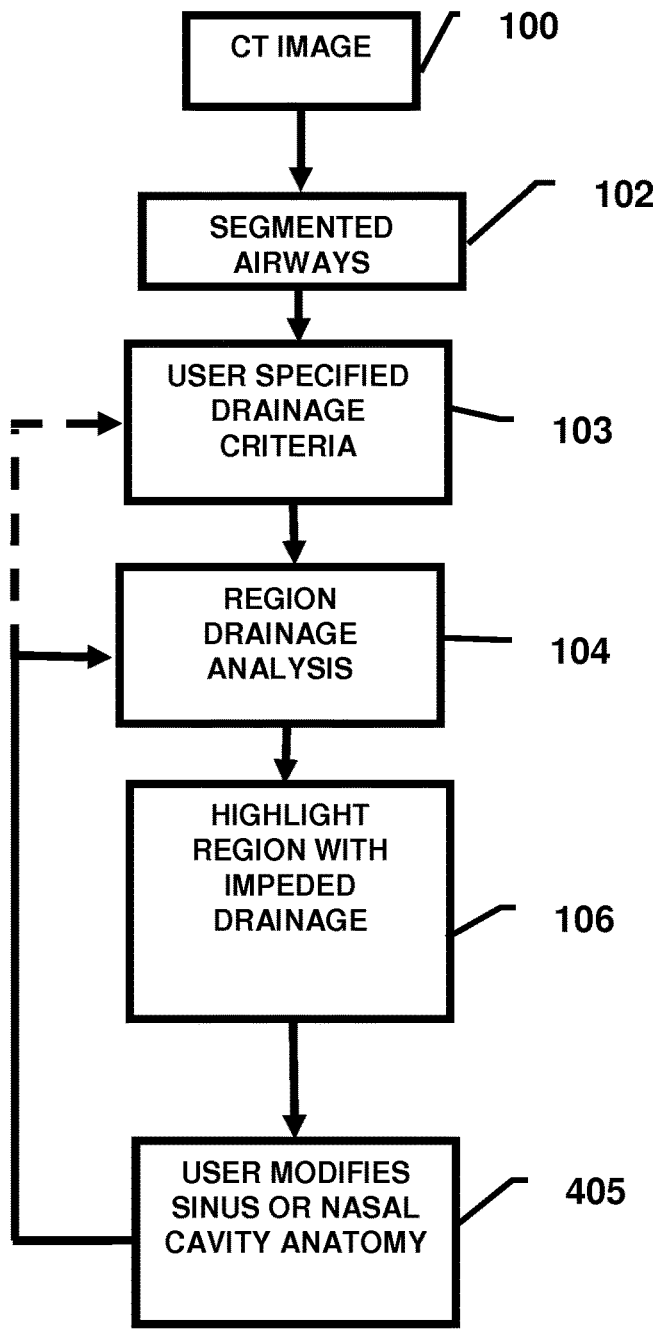
FIG. 4 is a logic flow diagram that shows optional user modification for drainage analysis processing.

The logic flow diagram of FIG. 4 shows an added user input step 405 used in an alternate embodiment of the present invention, allowing the user to provide input that improves segmentation, including edits to the class map, for example. In step 405, the user provides instructions that modify the display of anatomy of the nasal region in some way. Modifications can be indicated interactively by viewer instructions entered with reference to a displayed rendering of the CT slices in a coronal, axial, sagittal, or other view. User input instructions can be entered using a pointer device, such as a mouse or joystick, for example, or using touch screen input. Alternatively, the user may interact with the system using a 3D rendering of the nasal region. For example, in step 405 the user may enter instructions that indicate that an ostium of the left maxillary sinus is blocked.

Upon receiving user instructions in step 405 of FIG. 4, the system returns to step 104 to re-calculate and re-determine regions between which drainage paths exist. Alternatively, as shown in FIG. 4, processing returns to step 103 in which the drainage path constriction criteria for detection and display are modified. For example, the left maxillary sinus may initially display in the same color as the nasal cavity. Then, for example, in step 405, if the user indicates constriction or blockage of the maxillary ostium, the color of the maxillary sinus may change. Otherwise, the existence of auxiliary ostia is indicated. In step 405, the user may also indicate other modifications including, but not limited to, the removal of sinus cells, bone, and other tissue from display. This may be helpful, for example, to allow better visibility of obscured features along the airway path.

Figure 5:
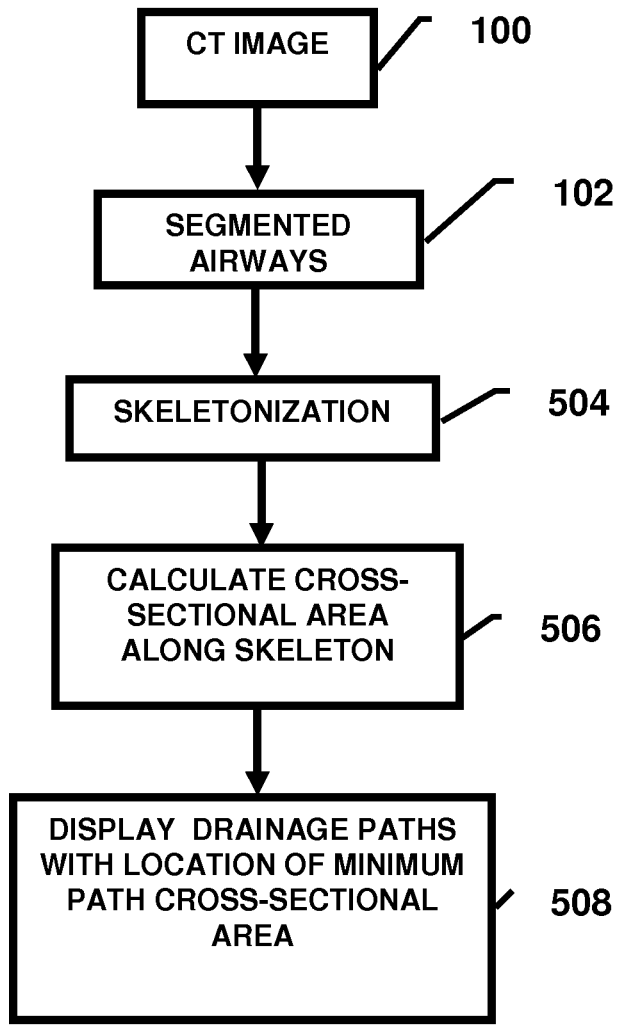
FIG. 5 is a logic flow diagram showing alternate skeletonization processing for airway detection and display.

The logic flow diagram of FIG. 5 shows processing according to an alternate embodiment of the present invention, using skeletonization. In a skeletonization step 504, the segmented airways from step 102 are skeletonized. This presents a display that more clearly identifies the airway path and distinguishes the airway path from other image features. For example, mucous drainage paths between a sinus cell and the nasal cavity are identified. Formally, skeletonization of a 3D object is defined using the loci of centers of maximally inscribed spheres. In effect, the skeleton is comprised of medial lines that outline the shape of the object. Skeletonization methods that preserve the topology of the object may also contain pockets that enclose internal cavities. The methods used for skeletonization may utilize any of the techniques that are known in the art for isolating well-defined uniform structures from other 3-D image content, including boundary peeling, thinning, erosion, and distance transform, for example. In a calculation step 506, the cross-sectional area of the airway is calculated along the skeleton. This cross-sectional area may be reported to the user in various ways, such as in terms of area, effective radius, effective diameter, or using any other metric that expresses the cross-sectional area. In a display step 508, paths within the airways are highlighted, displayed to the user with important locations indicated. Important locations can include, but are not limited to, locations of global or local minimum cross-sectional area that may occur at sinus ostia or locations at which a drainage path is restricted. In addition, the system displays a virtual endoscopic view at important path locations.

Figure 6:
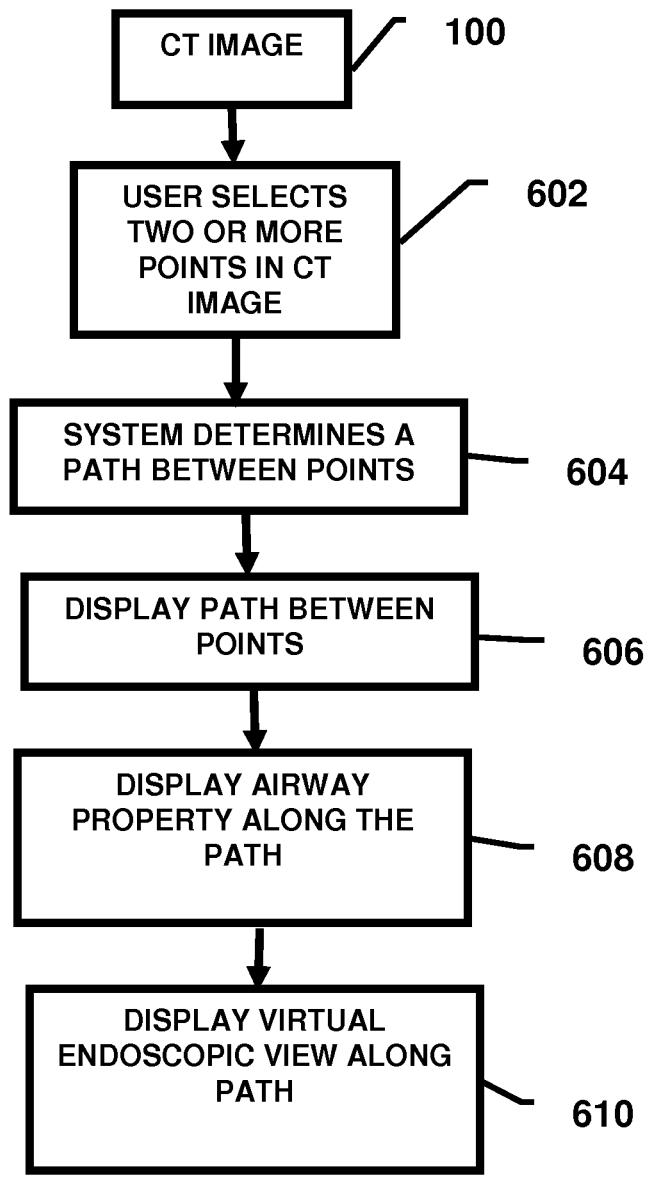
FIG. 6 is a logic flow diagram for specifying and displaying an airway path according to an embodiment of the present invention.

Another aspect of this invention is shown in FIG. 6. In a selection step 602, the user selects two or more points in the image. The user instruction for this purpose may select the points using interaction with the CT slices or with a 3D rendering of the nasal region. The user may also select the points from a list of anatomical features. For example, the user may indicate a point in the throat and another point in the right frontal sinus. In a path determination step 604, the system determines a path between the points and displays the path to the user. In some cases, the system may also inform the user that no path could be found.

For step 604 in FIG. 6, a path-finding algorithm, such as Dijkstra's algorithm, well known to those skilled in the image processing arts, is used for path determination according to one embodiment of the present invention. The path finding algorithm can determine a lowest cost path based on several definitions of cost. For example, the cost of a path may be based on its length, on its minimum cross-sectional area, on its average cross-section area, on a combination of cross-sectional area and length, or on other path properties. Of special relevance are properties that relate to the flow and drainage of mucus. In a display step 606, the system displays the path to the user by highlighting or annotating a 3D rendering of the CT data and/or by highlighting or annotation of the CT slices. In a display step 608, characteristics of the path such as the effective diameter at each point along the path are displayed to the user in graphical or tabular form. The system also displays to the user a virtual endoscopic view at one or more locations on the path as indicated by a display step 610. Examples and more detailed description of a virtual endoscopic view are given subsequently.

Figure 7:
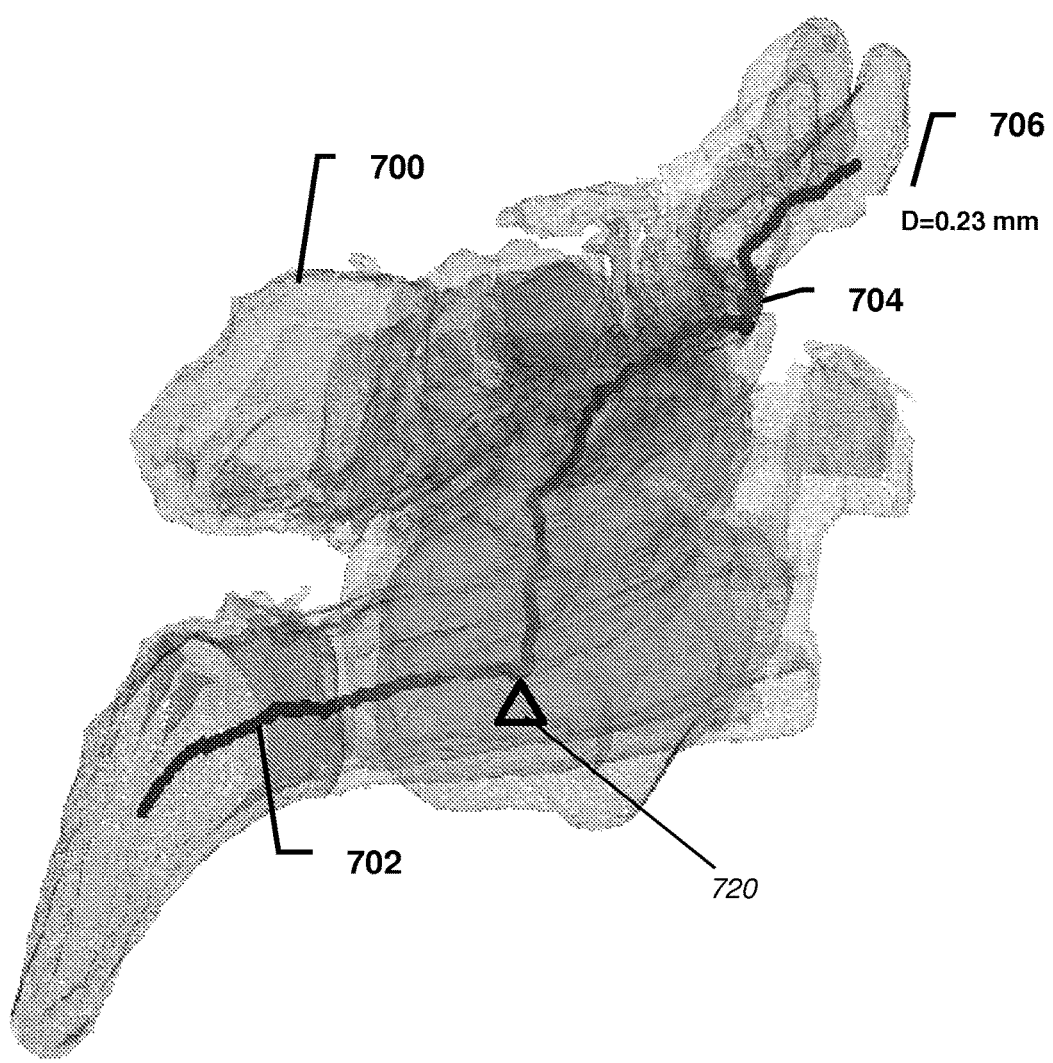
FIG. 7 shows a segmented airway with a highlighted path.

By way of example, FIG. 7 illustrates displayed results of the process outlined in FIG. 6. In the volume display of FIG. 7, a segmented airway 700 displays, showing a calculated path 702 between identified points in the right frontal sinus and throat. A symbol 704 is located at the position along the skeleton at which the cross-sectional area of the path is a minimum. In addition to symbol 704, numerical values display to convey additional information. In the example shown, the effective diameter at the location of the symbol 704 is provided by a numerical annotation 706.

In addition to identifying areas of constriction, embodiments of the present invention also analyze path 702 for locations of high curvature. This indicates where endoscopy would be blocked or difficult, such as near a symbol 720 in FIG. 7.

Figure 8:
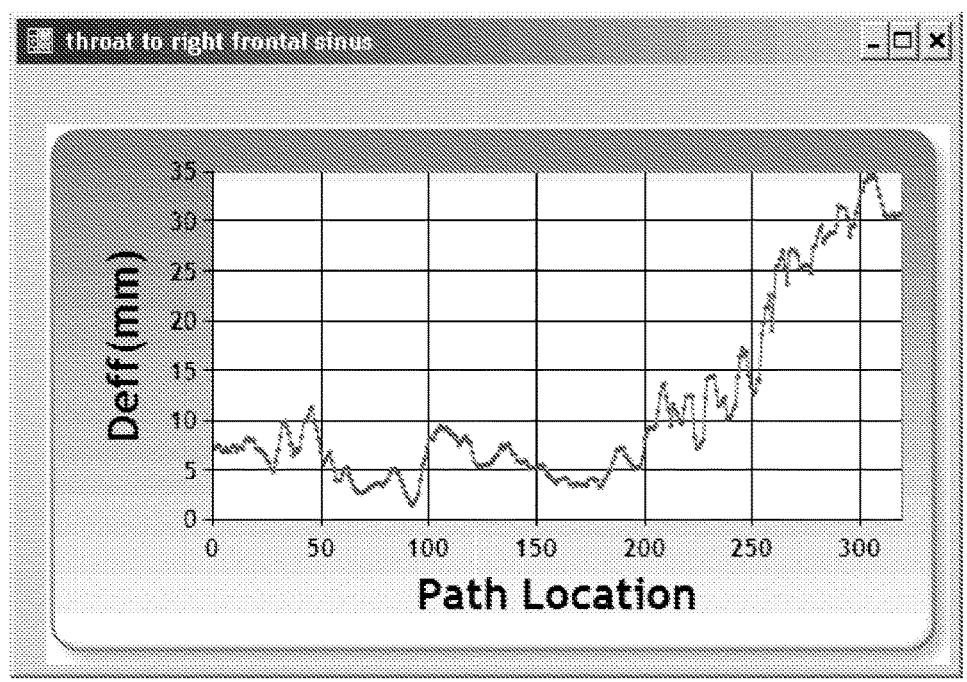
FIG. 8 shows a user interface window for showing cross-sectional path information.

A user interface window 710 in FIG. 8 shows an example of path cross-sectional area information shown in a graphical fashion for an automatically determined path between a point in a frontal sinus and the throat. The decrease in effective path diameter (Deff) at locations in the frontal recess is indicated.

In addition to displaying calculations related to path dimensions, other information can also be provided in graphical form. This includes drainage information relative to an airway path. Related information for drainage also includes curvature data for a point in the path. Curvature can be expressed in terms of radius and arc length, for example, or can be expressed in terms of a curvature index or other computed value.

Figure 9:
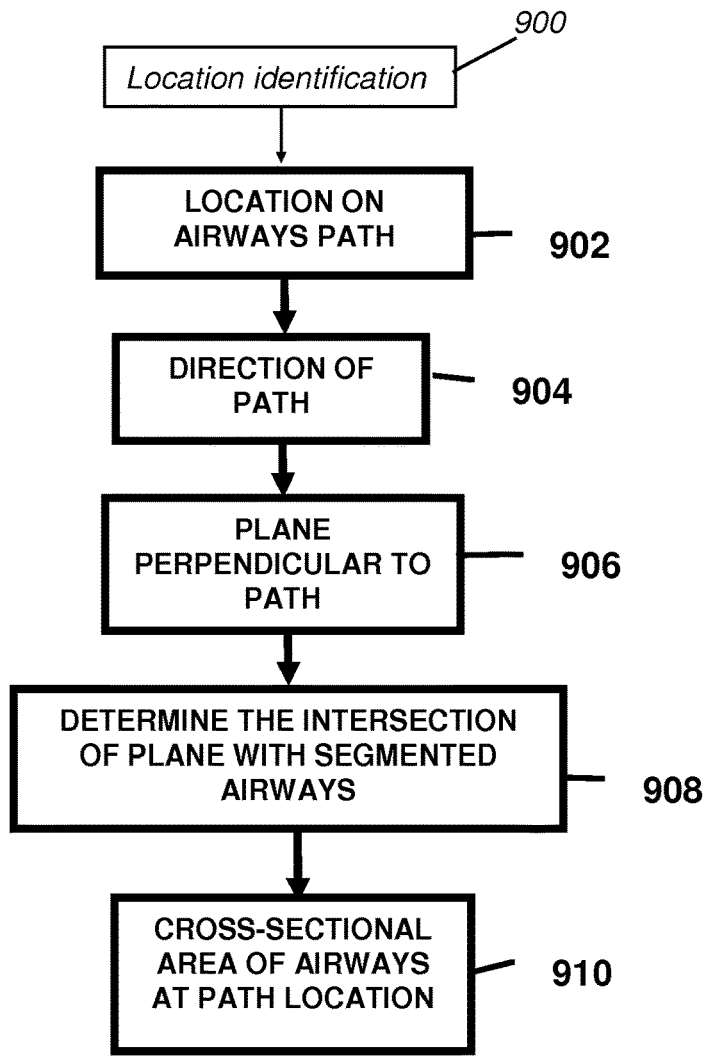
FIG. 9 is a logic flow diagram showing how the cross-sectional area of the airway path can be computed according to an embodiment of the present invention.

FIG. 9 shows a method that is used by the system to determine the cross-sectional area of an airway path. In a location identification step 900, a location 902 on a path in the airways is identified. In practice, this location may be within the skeleton, such as between two locations where drainage between the locations is of interest. In a direction determination step 904 the direction of the path is determined at the location 902 along the airway path. In a plane determination step 906, the plane that is perpendicular to the path direction from step 904 at path location 902 is determined. Next, in an intersection determination step 908, the intersection of the segmented airways and this plane is determined. This intersection may consist of one or more disconnected regions. The connected region in the plane that contains the path point 902 is the part of the segmented airways that, in a cross-sectional area definition step 910, defines the cross-sectional area of the airway at location 902. This connected region is determined by tracing rays that are confined to plane 906 from location 902. Each ray is traced until it exits the segmented airways. The length of the ray is the radius of the airway in the ray's direction. The cross-sectional area of the airways at path location 902 is calculated by tracing rays in a 360 degree circle. The steps in FIG. 9 repeat as needed to determine the cross-sectional area along the path. This also provides data for estimating the volume of the corresponding path.

Figure 10:
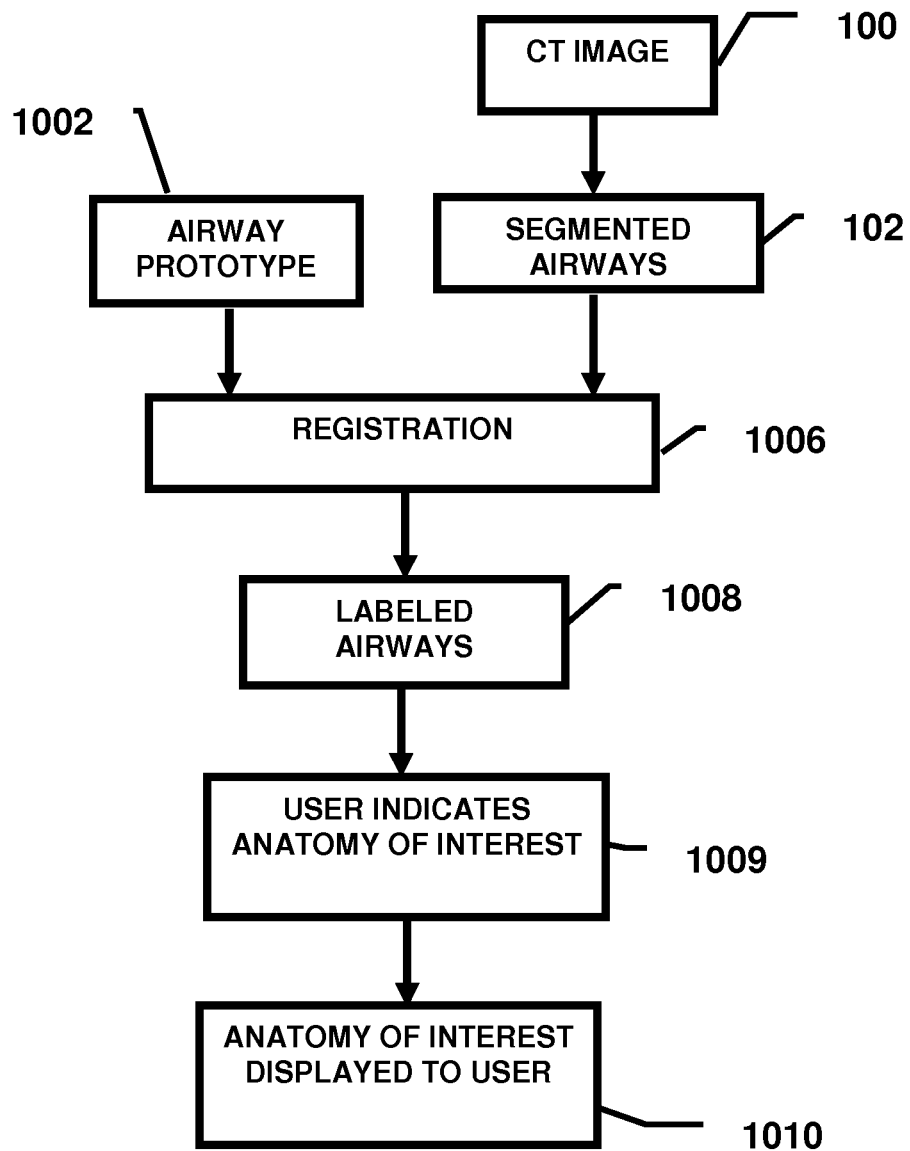
FIG. 10 is a logic flow diagram showing how atlas registration is used for labeling of airway portions.

The logic flow diagram of FIG. 10 shows another aspect of an embodiment of the present invention, using comparison between the airways volume image and an atlas or other prototype. In a registration step 1006, an airways atlas or other prototype 1002, is registered with the segmented airways of the patient from step 102. According to an embodiment of the present invention, the prototype that is used is an atlas that has been generated as a segmented airway for which the location of significant anatomy has been labeled. An atlas is a 3-D model typically generated from statistical data obtained using a number of samples. Labeling is generally performed manually by a person who has thorough knowledge of the anatomy of the paranasal sinus region. By the registration process of step 1006, the atlas is transformed to match the patient's airways so that the labels in the atlas can be transferred to the patient's airways. As a result, the anatomy of the patient's airways is determined.

Registration step 1006 in FIG. 10 may include both rigid and non-rigid registration. Rigid registration uses translation and rotation to match the atlas or other prototype and segmented airways. Scaling is also added to translation and rotation because the prototype and patient's airways may be of different size. When scaling and shears are added in addition to translation and rotation, the registration is termed affine registration. Rigid or affine registration is not always sufficient to match an atlas with the patient's airways because there can be considerable variation in airways anatomy. For this reason, step 1006 also includes non-rigid registration utilities. In non-rigid registration, the atlas or other prototype may be deformed when it is mapped to the patient's airways. Non-rigid registration usually involves determining corresponding points between the atlas and patient's airways and calculating an optimal mapping that transforms a set of atlas points to their respective corresponding points in the patient's airways. Generally, the mapping must satisfy continuity conditions and other constraints that prevent a perfect mapping of the prototype's points to their corresponding points in the patient's airways. Step 1006 may use any non-rigid registration method known in the art. Non-rigid registration using splines, correlation, Fourier, mutual information, relaxation, elastic, and wavelet methods can be used for this function. In a labeling step 1008 the patient's airways are labeled by transfer of labels from the registered atlas. After this step, the patient's airways with labeled anatomy can be displayed in a display step 1010.

Additional capabilities of the system are illustrated in a step 1009 of FIG. 10 in which the user indicates anatomy of interest. This could be accomplished in many ways, such as by selection from a list, by audible prompt, or by pointing to locations on displayed image slices or on a 3D rendering of the image. In step 1010, the system displays the anatomy of interest to the user. The anatomy of interest may display as a close-up or zoom-in of a 3D rendering and/or CT slices, a virtual endoscopic view, or a graphical representation. The system also displays characteristics of the anatomy of interest including, but not limited to, the volume of air and the natural volume as determined by the bony boundary of the anatomy. Examples of anatomy of interest include, but are not limited to, the location of sphenoid, frontal, maxillary, and ethmoid sinus cells. In addition, the system automatically locates, marks the location of, and provides zoomed views of the infraobital nerve, ethmoidal artery, orbital fissure, optic nerve, vidian canal, and carotid arteries, and other nerves, arteries, and critical anatomy.

A related use of the atlas or other prototype helps to identify anatomical irregularities or anomalies for a particular patient. This can be detected for example, when methods for fitting the anatomy to the atlas fail to provide a match to within predetermined thresholds or when a comparison of atlas fitting is made among atlases with different anatomical variations. Using an atlas with associated processing, the system is able to determine features such as septal deviations which result in impaired sinus drainage. The system is also able to indicate the presence and location of agger nasi cells, supraorbital cells, and type 1-4 frontal cells which affect mucus drainage and need to be considered during sinus surgery.

Figure 11:
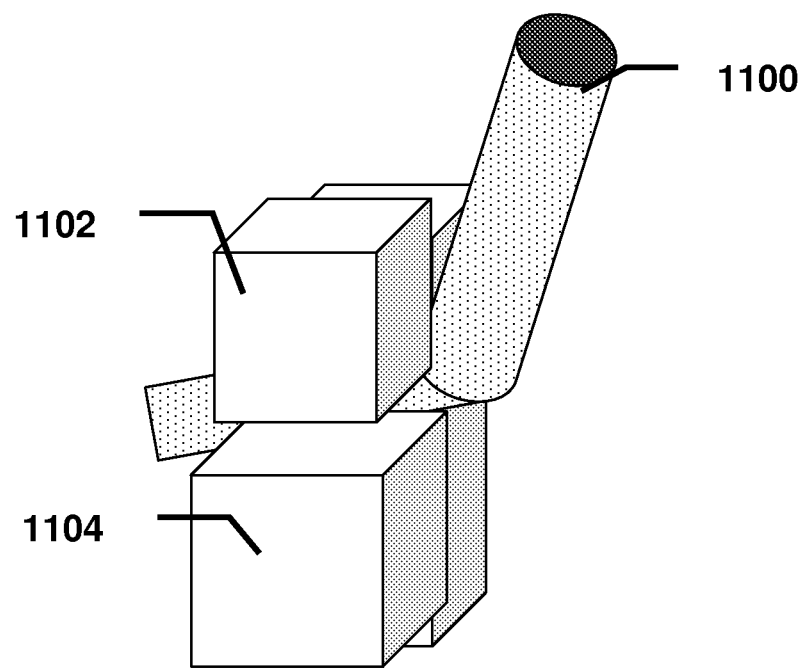
FIG. 11 shows anatomy of interest displayed to the user as a graphical representation of anatomical structures.

By way of example, FIG. 11 shows anatomy of interest and anatomical variations displayed to the user as a graphical representation of anatomical structures. In this case, the anatomy of interest is the frontal sinus drainage path 1100. The graphic representation shows that drainage occurs around the agger nasi cell 1104 and frontal cell of the ethmoid sinus 1102. This type of symbolic representation can be helpful for providing summary details to a practitioner in more generalized form.

Figure 12:
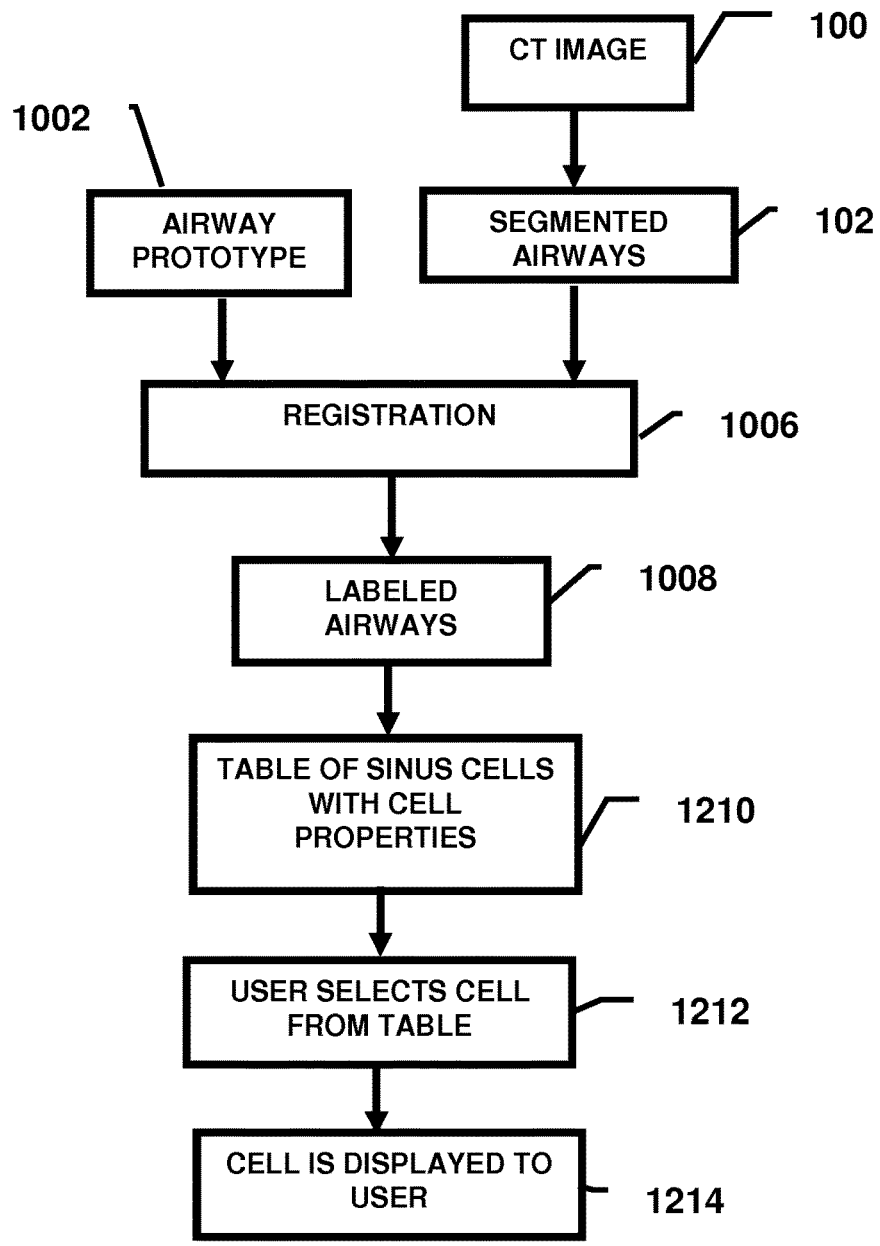
FIG. 12 is a logic flow diagram that shows how a table of sinus cells is developed and used according to an embodiment of the present invention.

Another aspect of this invention is shown in the logic flow diagram of FIG. 12. In a table generation step 1210, the system produces a table of sinus cells that includes information on cell properties. Properties include, but are not limited to, location of the cell, the bone in which the cell resides, and cell volume. The cell volume may include the air volume of the cell. The cell volume may also include the "natural" volume of the cell as determined by bone boundaries. If the air volume of the cell differs from its natural volume, the presence of mucous, polyps, or an infection is indicated. In a selection step 1212, the user selects one or more cells from the table of sinus cells. Then, in a display step 1214, the system displays the selected sinus cells to the user. The cells may be displayed as a 3D rendering, CT slices, or as a virtual endoscopic view. Cells not selected can be invisible or shown in outline, for example.

Some portions of the detailed description given hereinabove are presented in terms of algorithms and symbolic representations of operations on data bits within a computer memory. These algorithmic descriptions and representations are the means used by those skilled in the data processing arts to more effectively convey the substance of their work to others skilled in the art. An algorithm is here, and generally, conceived to be a self-consistent sequence of steps (instructions) leading to a desired result. The algorithm steps are those requiring physical manipulations of physical quantities. Usually, though not necessarily, these quantities take the form of electrical, magnetic or optical signals capable of being stored, transferred, combined, compared and otherwise manipulated.

In the context of the present disclosure, the term "computer" can be broadly interpreted to describe any type of computer, computer system, or logic processor hardware that is capable of executing programmed instructions for the image processing and display functions described herein. Unless specifically stated otherwise as apparent from the preceding discussion, it is appreciated that throughout the description, discussions utilizing terms such as "processing" or "computing" or "calculating" or "determining" or "displaying" or "determining" or the like, refer to the action and processes of a computer system, or workstation or similar electronic computing device that manipulates and transforms data represented as physical (electronic) quantities within the computer system memories or registers or other such information storage, transmission or display devices.

Certain aspects of the present invention include process steps and instructions described herein in the form of algorithms or image processing utilities. It should be noted that the process steps and instructions of the present invention could be embodied in software, firmware or hardware, and when embodied in software, could be downloaded to reside on and be operated from different computer processing platforms used by a variety of operating systems.

According to one embodiment of the present invention, there is provided a system for displaying paranasal and sinus features of a patient, the system comprising: a display and a computer processor for executing executable computer program code; a computer-accessible storage medium containing the executable computer program instructions for performing a method comprising acquiring a volume image of a paranasal region of the patient; identifying one or more airways within the paranasal region; displaying at least the one or more airways on the display; and, highlighting portions of the displayed one or more airways that are constricted below a predetermined value.

Thus, the present invention also relates to an apparatus for performing the operations herein. This apparatus may be a processor specially constructed for the required purposes, or it may comprise a general-purpose computer selectively activated or reconfigured by a computer program stored in the computer. Such a computer program may be stored in a computer readable storage medium, such as, but not limited to, any type of disk including magnetic disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus to practice the method according to the present invention. Furthermore, the computer(s) referred to in the specification may include a single processor or may use architectures that employ multiple processors for increased speed and computing capability.

Figure 13:
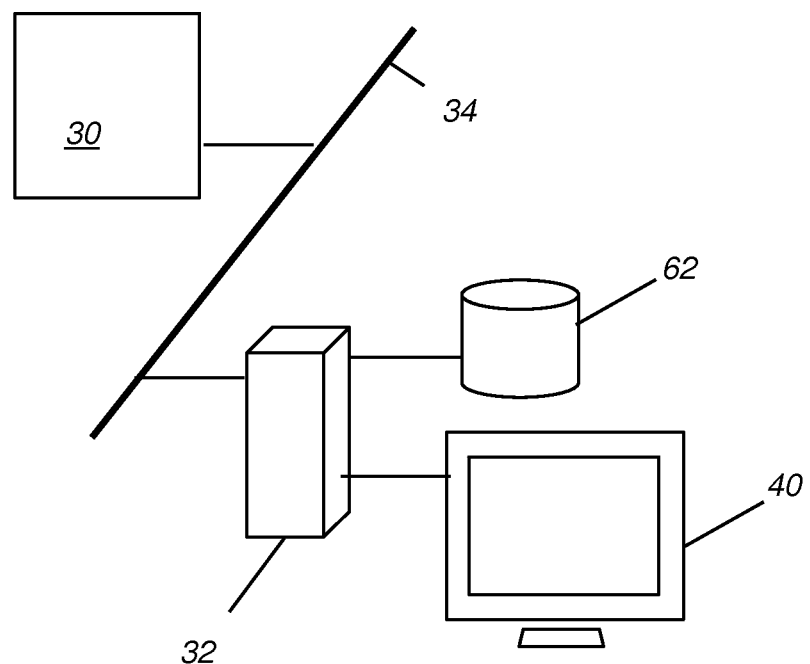
FIG. 13 is a schematic block diagram that shows a processor apparatus for performing the processing and display functions of the present invention.

The schematic block diagram of FIG. 13 shows a processor apparatus for performing the processing and display functions of the present invention. An imaging apparatus 30 acquires the CT or other volume image of the paranasal sinus region, including nasal cavity areas. A host computer 32, typically connected along a network 34 obtains the acquired volume image for processing and display on a display monitor 40. Host computer 32 stores the received image data in a computer-accessible electronic memory 62 for subsequent delay and processing.

A variety of user interface options is available at display monitor 40, enabling the viewer to more readily identify features of the paranasal sinus region and related sinus cavities and to obtain information related to path blockage, connectedness, and relative diameter at any point. Among optional user interface options for controlling how passages and other features are displayed are the following:

(i) select colors or other presentation aspects such as gray scale or intensity for the airway path as well as for highlighting identified features that form the paranasal sinus region and related sinus cavities;

(ii) enable or disable path display, for all or part of the paranasal sinus region;

(iii) enable or disable display of any portion or region of interest of the paranasal sinus region structures;

(iv) select and highlight a portion or region of interest, such as using a mouse, touch screen, or menu selection;

(v) display volume measurement, either at any point along the path, at any region of interest, within any specified chamber or cavity, between two points along the path, or for all features that are currently displayed;

(vi) select colors for indicating path blockage or other conditions, such as selecting a green color to indicate full blockage, a yellow color to indicate a point in the path with diameter less than 1 mm, and so on;

(vii) specify animation or other highlighting in order to better show features and passages displayed;

(viii) image capture, so that a hard copy image from a particular viewpoint can be printed; and (ix) adjustment capability, such as using a slider or control knob to adjust threshold values for display in different colors.

According to an alternate embodiment of the present invention, an optional autozoom capability is provided to help the practitioner to readily display a portion of the sinus anatomy at a higher magnification. Selection of particular anatomy for autozoom display can be performed using a menu that lists portions or cells of the sinus anatomy. For example, FIG. 14C shows a user interface for automatically locating and zooming to selected anatomy. A 3D rendering of the airways is displayed as a view 53 to the user. The user selects from list 51 of anatomical features. In this example the left maxillary sinus is selected. As a result of the selection by the user, the system displays an axial 57, coronal 55, and sagittal 59 zoomed view of the selected anatomy.

It is noted that the term "memory", in the context of the present disclosure, can refer to any type of temporary or more enduring data storage workspace used for storing and operating upon image data in a computer system. The memory could be, for example, a long-term storage medium such as magnetic or optical storage. Alternately, the memory could be an electronic circuit, such as random-access memory (RAM) that is used as a temporary buffer or workspace by a microprocessor or other control logic processor device. Display data, for example, is typically stored in a temporary buffer and refreshed as needed in order to provide displayed data. This temporary storage buffer can also be considered to be a memory. Memory can be volatile, non-volatile, or a hybrid combination of volatile and non-volatile types.

FIG. 13 is shown by way of example to illustrate one type of computer apparatus for performing the processing of the present invention. It should be noted that algorithms and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description given earlier.

Figure 14A:
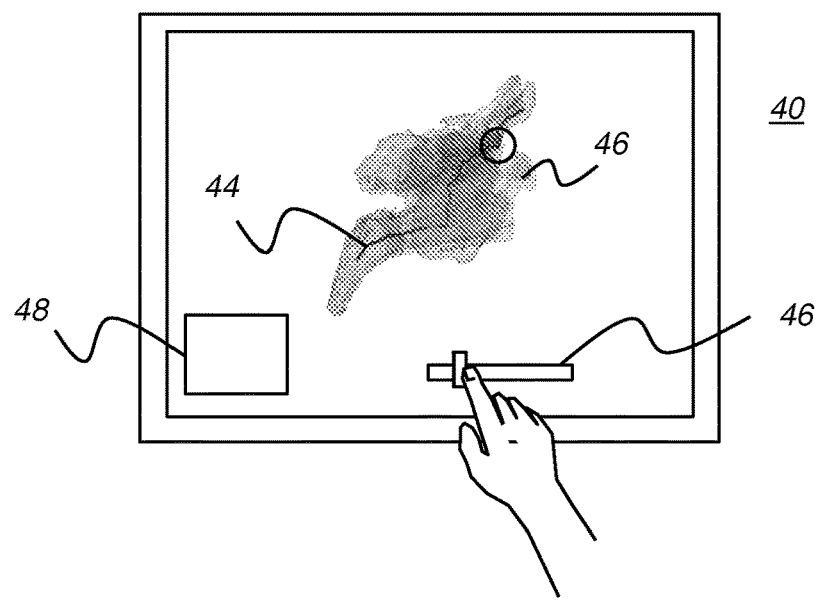
FIGS. 14A and 14B show examples of a user interface provided for entry of user instructions.
Figure 14B:
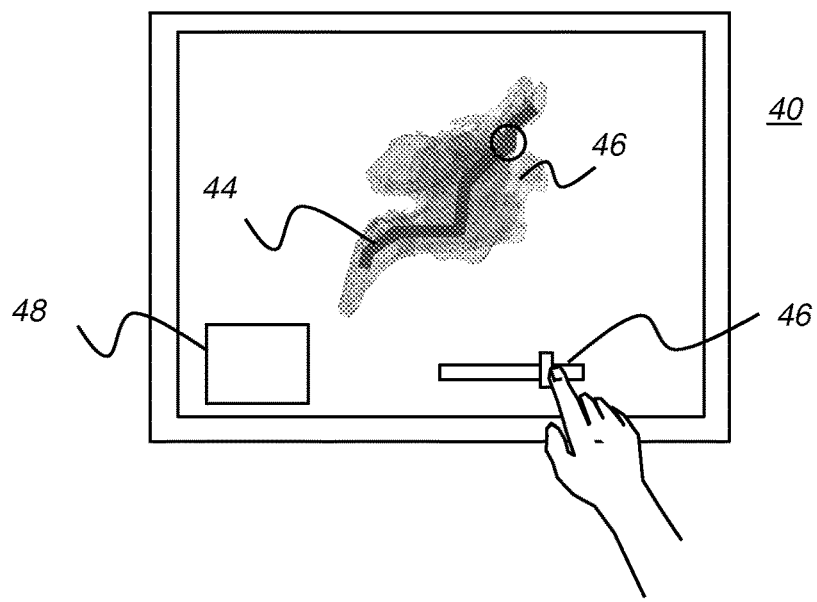
Figure 14C:
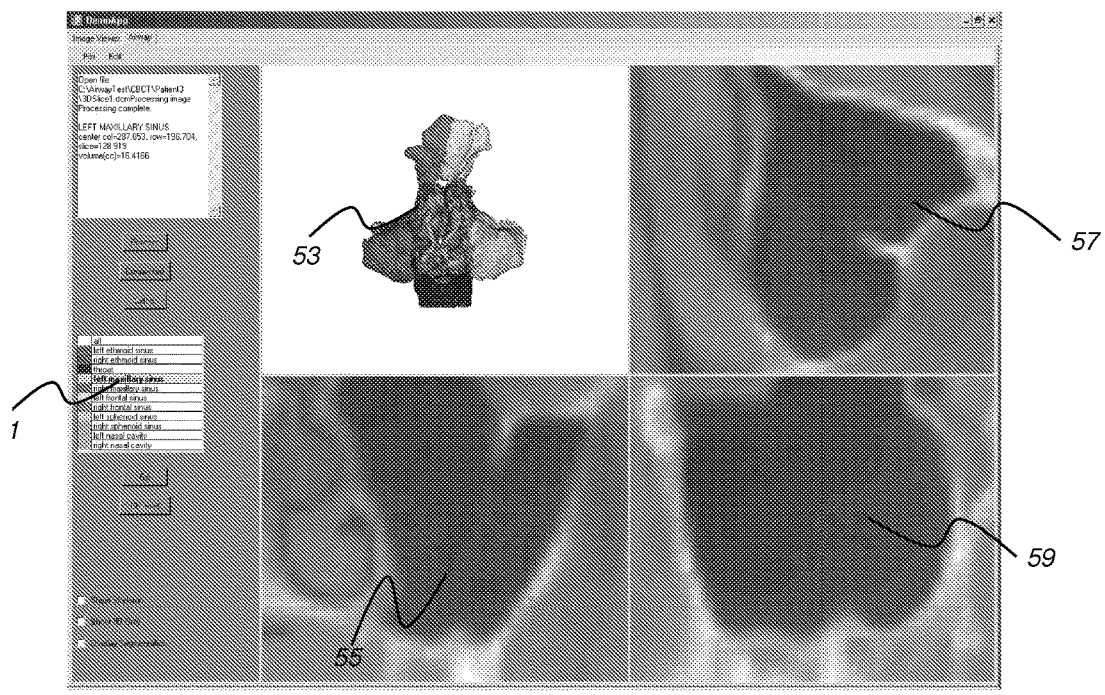
FIG. 14C shows examples of a user interface provided for auto locate and zoom of an anatomical feature that is indicated by the user.

FIGS. 14A and 14B show a user interface provided on display monitor 40 for entry of user instructions that can affect the display of a volume image 42 of paranasal region structures and the airway path 44. A user control 46, such as a slider as shown, enables the user to adjust the visibility of airway path 44 or of related features. A menu 48 provides functions such as color selection and enable/disable capabilities for display of various anatomical and airway features as well as for entry of parameters for display.

Figure 15:
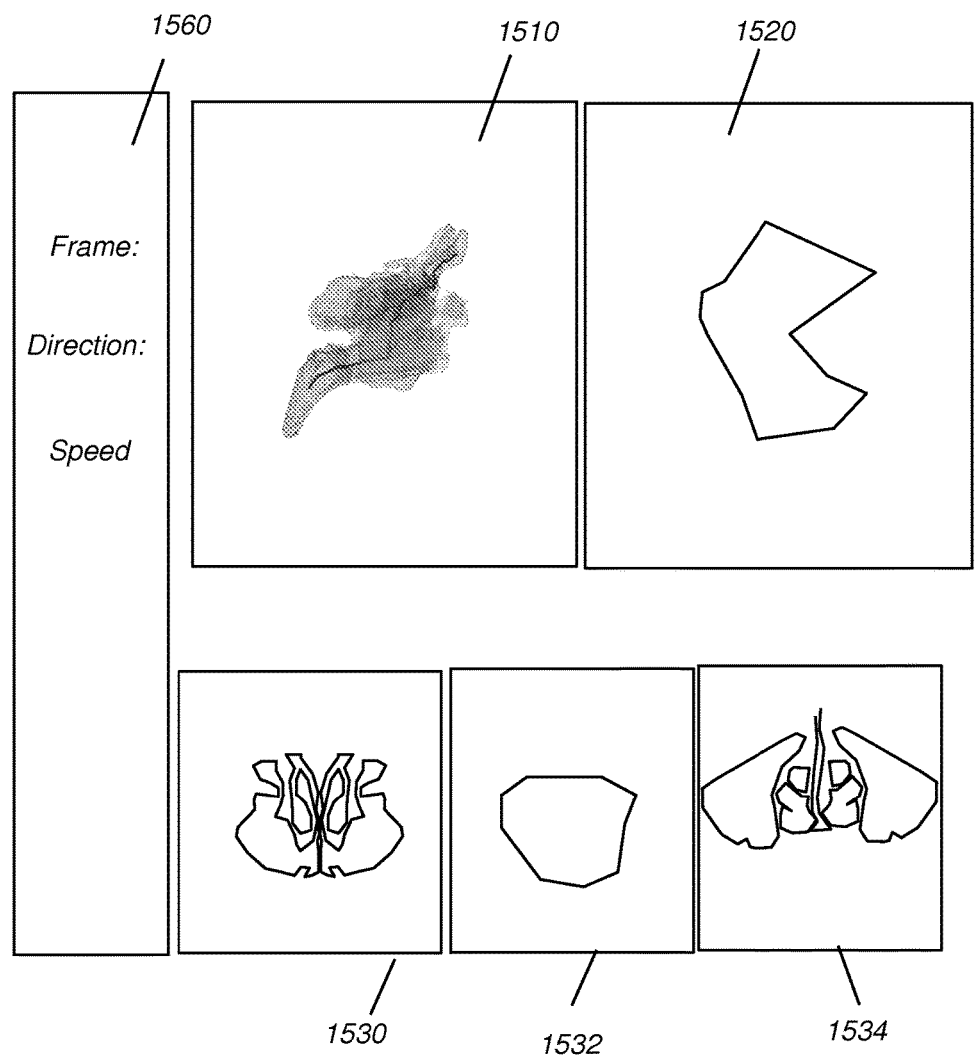
FIG. 15 shows a view of a virtual endoscopic interface according to an embodiment of the present invention.

As noted earlier, the operator interface may also present a virtual endoscopic view. To obtain a virtual endoscopic view, control logic replicates the field of view that would be obtained using an endoscopic probe passed through airway channels. According to an embodiment of the present invention, the virtual endoscopy view is displayed to the user along with a 3D rendering of the image and axial, sagittal, and coronal slices. The location of the endoscopic view is indicated in the 3D rendering and slices. Also, the direction of the view is indicated in the 3D rendering. FIG. 15 shows a view of the virtual endoscopic interface, with sections of the display screen shown in block form. A side view 1510 shows a volume rendering of a portion of the sinus passage and represents the relative, computed position of the virtual endoscopic probe. Axial, sagittal, and coronal views 1530, 1532, and 1534, respectively, are provided for the sinus path at the position of the virtual endoscopic probe. An endoscopic view 1520 is then reconstructed using the corresponding volume information. A control panel 1560 provides various utilities for controlling the presentation of this virtual information. This can include setting variables that control speed of refresh of the display for advancing the virtual probe, forward or reversed direction of the probe, and frame or slice within a volume.

The invention claimed is:

1. A method for analyzing and displaying constricted regions of a paranasal sinus region of a patient, the method executed at least in part on a processor, comprising:
   acquiring volume image data of the paranasal sinus region of the patient;
   generating a volume image of the paranasal sinus region from the volume image data;
   segmenting 3D airways from the generated volume image of the paranasal sinus region;
   automatically identifying, by the processor, connected 3D airways that pass between a frontal paranasal sinus to the throat, within the segmented paranasal sinus region from the volume image, where the connected 3D airways include frontal sinus, frontal ostium, superior cavity, middle meatus and nasal cavity;
   displaying the connected 3D airways within said volume image; and
   highlighting one or more portions of the displayed connected 3D airways that are constricted below a predetermined value along said each of the connected 3D airways.

2. The method of claim 1 wherein acquiring the volume image data comprises acquiring a cone-beam computerized tomography image.

3. The method of claim 1 segmenting 3D airways of the acquired volume image comprises assignment of a class to a voxel, and wherein the assignment is according to one or more code values of one or more neighboring voxels in the volume image.

4. The method of claim 1 segmenting 3D airways of the acquired volume image comprises assignment of a class to a voxel, and wherein the assignment is according to the class assignment of one or more neighboring voxels in the volume image.

5. The method of claim 1 wherein displaying the connected 3D airways further comprises displaying one or more features of the paranasal sinus region of the patient.

6. The method of claim 1 wherein identifying the connected 3D airways comprises mapping a prototype of the paranasal sinus region to the volume image, further comprising identifying one or more anatomical anomalies of the patient according to the prototype.

7. The method of claim 1 wherein highlighting the one or more portions of the displayed connected 3D airways comprises using color.

8. The method of claim 1 further comprising modifying portions of the displayed connected 3D airways in response to a user instruction, where the user instruction is entered using an on-screen control element on a display, where the user instruction relates to drainage criteria for the connected 3D airways.

9. The method of claim 1 wherein displaying the connected 3D airways further comprises displaying cross-sectional area as a quantititative value.

10. The method of claim 1 wherein a cross-sectional area calculation is provided according to a user selection of a location along the connected 3D airways.

11. The method of claim 1 wherein identifying the connected 3D airways further comprises identifying the connected 3D airways between first and second user-specified locations.

12. The method of claim 11 wherein displaying the connected 3D airways further comprises displaying a graph that shows cross-sectional area.

13. The method of claim 11 wherein displaying the connected 3D airways further comprises displaying information that relates to drainage capacity or information that relates to curvature of the connected 3D airways.

14. The method of claim 1 wherein displaying the connected 3D airways comprises displaying a graphical representation of anatomical structures.

15. The method of claim 1 further comprising providing an auto-zoom function that shows a magnified view of a specified portion of the paranasal sinus region in response to an operator instruction.

16. The method of claim 1 further comprising providing an endoscopic view that corresponds to a selected location along the connected 3D airways.

17. A method for displaying a paranasal sinus region of a patient, comprising:
  acquiring a volume image of the paranasal sinus region of the patient obtained from a computerized tomography apparatus;
  segmenting airways from the acquired volume image of the paranasal sinus region;
  automatically identifying airways that include paranasal sinuses and nasal cavity within the volume image;
  automatically deterimine condition and connections of the airways that include the paranasal sinuses and the nasal cavity;
  displaying the airways that include the paranasal sinuses and the nasal cavity; and
  displaying preselected drainage information for the displayed airways.

18. The method of claim 17 wherein displaying the information that is related to airway anatomy comprises displaying one or more symbols.

19. The method of claim 17 wherein displaying the airways further comprises displaying cross-sectional area as a quantitative amount.

20. The method of claim 17 wherein identifying the airways further comprises mapping an atlas of the paranasal sinus region to the volume image.

21. The method of claim 17 further comprising highlighting one or more portions of the displayed airways using color.

22. A system for displaying a paranasal sinus region of a patient, the system comprising:
  a display and a computer processor for executing executable computer program instructions; and
  a computer-accessible storage medium containing the executable computer program instructions for performing a method comprising:
    acquiring volume image of the paranasal sinus region of the patient;
    segmenting airways from the acquired volume image of the paranasal sinus region;
    selecting a first point in a volume image of the paranasal sinus region, where the first point is within one anatomical feature of a group of anatomical features in the volume image of the paranasal sinus region;
    selecting a second point in a volume image of the paranasal sinus region, where the second point is within a remaining non-selected anatomical feature in the group of anatomical features in the volume image of the paranasal sinus region;
    automatically identifying by the computer processor, connected 3D airways between said selected two points; and
    displaying the connected airways between said selected two points with cross-sectional information of each connected airway.

23. The system of claim 22, where an automatically identified path is based on path length or path cross-sectional area.

* * * * *